US006507360B1

(12) United States Patent
Spapens

(10) Patent No.: US 6,507,360 B1
(45) Date of Patent: Jan. 14, 2003

(54) METHOD OF MANUFACTURING A CATHODE RAY TUBE, IN WHICH A DISPLAY SCREEN IS INSPECTED

(75) Inventor: Wilhelmus G. M. Spapens, Eindhoven (NL)

(73) Assignee: Koninklijke Philips Electronics N.V., Eindhoven (NL)

( * ) Notice: Subject to any disclaimer, the term of this patent is extended or adjusted under 35 U.S.C. 154(b) by 0 days.

(21) Appl. No.: 09/443,562

(22) Filed: Nov. 19, 1999

(30) Foreign Application Priority Data

Nov. 25, 1998 (EP) .............................. 98203983

(51) Int. Cl.[7] .................................. H04N 5/64
(52) U.S. Cl. ................. 348/189; 348/190; 348/191; 348/326; 348/333.12; 348/745; 348/806
(58) Field of Search ....................... 348/189, 190, 348/191, 325, 326, 333.12, 744, 745, 763, 776, 781, 782, 785, 786, 805, 806, 807, 811; 356/237.1, 237.6; H04N 5/64, 9/16, 17/00

(56) References Cited

U.S. PATENT DOCUMENTS 4,845,558 A    7/1989   Tsai et al.
5,790,913 A  * 8/1998   Roberts, Jr. et al. ......... 348/128
5,847,822 A  * 12/1998  Suiura et al. ................ 356/239
6,014,168 A  * 1/2000   Webb et al. ................. 348/190
6,118,113 A  * 9/2000   Hibbard et al. ............. 250/205

OTHER PUBLICATIONS

Japanese Abstract No. 53–48589, "Inspecting Apparatus of Braun Tube Panel", Feb. 5, 1978, International Class G01N21 32.

* cited by examiner

Primary Examiner—John Miller
Assistant Examiner—Brian Yenke

(57) ABSTRACT

The display screen of a cathode ray tube is inspected. The arrangement with which the display screen is inspected comprises an adjustable mirror arrangement and an adjustable focal lens. By means of the arrangement, a set of sub-images is picked up, which sub-images are analyzed. The movable elements of the mirror arrangement and the focal lens are not moved during the image pick-up operation so as not to disturb the measurements. The difference data between picked-up images and standard images are generated in a unit, and errors are detected with reference to these difference data. These errors are preferably ordered as to magnitude and/or importance.

16 Claims, 7 Drawing Sheets

METHOD OF MANUFACTURING A CATHODE RAY TUBE, IN WHICH A DISPLAY SCREEN IS INSPECTED

BACKGROUND OF THE INVENTION

The invention relates to a method of manufacturing a cathode ray tube, which method comprises a step of inspecting a pattern provided on a display screen of or for a cathode ray tube.

BRIEF SUMMARY OF THE INVENTION

Cathode ray tubes are used, inter alia, for (color) display devices such as televisions and computer monitors.

A cathode ray tube comprises a display screen which has a plurality of patterns, for example, phosphor patterns or black matrix patterns. Errors in these patterns are visible in the image displayed by the cathode ray tube and may thus have the result that the display device does not satisfy the imposed quality requirements and is consequently unsalable and has to be rejected. It is therefore important to detect pattern errors at an early stage of manufacture in order to reduce the number of rejects and/or to be able to interfere with the manufacturing process at an early stage so as to reduce the number of errors. A method of the type described in the opening paragraph is known from the English-language abstract of Japanese patent application JP 53-48589. This abstract describes a method in which a movable mirror is arranged in the focus of a spherical display window (a display window whose shape can be described by one radius of curvature) of or for a cathode ray tube, which movable mirror images pixels of the frame line by line in a small aperture behind which a light detector is arranged. The data picked up by the light detector are applied to a processing unit.

Although inspection of a display screen is possible in this manner, this method has some shortcomings.

The method may be applicable for inspecting screens at random, but not in a production line or in large numbers. The reason is that this requires a long pick-up and processing time for all data of a display screen. Moreover, problems occur with regard to display screens having an aspherical shape or display screens having a large radius of curvature, because the distance between the display window and the mirror becomes large and thus the arrangement becomes large and occupies much space. As the distance between the display screen and optical elements such as mirrors and lenses becomes larger, the resolution of the arrangement (=the smallest detail which can still be distinguished) becomes smaller. This can be corrected by using larger mirrors or lenses but this has the drawback that the mass of the elements increases so that the inertia increases, making it more difficult to manufacture optical elements of high quality.

It is an object of the invention to provide a method of the type described in the opening paragraph, in which one or more of said problems or problems mentioned below is obviated.

To this end, the method according to the invention is characterized in that a set of sub-images of the display screen, which set preferably covers the display screen entirely, is guided towards a camera via an adjustable mirror arrangement and an adjustable focal length lens (hereinafter adjustable focal lens or focal lens), each sub-image being picked up with the mirror arrangement and the focal lens in a rest state, the data of each sub-image being applied to a processing unit in which difference data about differences between the picked-up image and a standard image are generated, said data being applied to a further processing unit.

By using an adjustable focal lens, each sub-image can be sharply imaged on pick-up element of the camera. Changes in the distance between the camera and the display screen can thus be compensated. The mirror arrangement and the focal lens is set to the envisaged position for each sub-image. Subsequently, the sub-image, thus with the mirror and the focal lens in the rest (non-moving) state is picked up.

A problem in picking up images is that vibrations which may result from moving parts can disturb the pick-up operation. A "flying-spot" method, i.e. a method in which measurements are performed while elements (such as mirrors) are moving, thus disturbs the pick-up operation. Such disturbances may result in "false" errors, i.e. errors are registered as a result of movements of elements of the measuring arrangements. "False" errors raise the number of rejects and may cause considerable damage. The occurrence of vibrations may be prevented, for example, by maintaining the speed at which elements are moved relatively low, but this means that the measuring time is relatively long. The consequences of vibrations may also be decreased, for example, by damping measures, but this has a cost-increasing effect.

In the method according to the invention, the movable elements such as the mirror arrangement and the focal lens do not move when the sub-images are being picked up. As compared with the known method, in which the mirror arrangement is placed in the focus of the display window, the method according to the invention provides the additional advantage that the distance between the mirror arrangement and the display screen can be reduced as a result of the use of the adjustable focal lens. Nowadays, display windows are used with radii of curvature of several meters (2–5 m). In the method according to the invention, the distance between the display screen and the mirror arrangement is preferably between 50 cm and 120 cm so that a considerably shorter distance between the display screen and the mirror arrangement is possible. Thus the ratio of screen radius of curvature to mirror-to-screen distance may be greater than 16:1. This shorter distance has two positive consequences.

The method occupies less space and the effects of vibration of the mirror arrangement on an image picked up by the camera are smaller.

The distance is preferably shorter than 120 cm. As the distance increases, the resolution decreases. The resolution is approximately proportional to the cross-section of the optical elements, divided by the square value of the distance. Relatively small optical elements may be used up to distances of approximately 120 cm.

The distance is preferably larger than 50 cm. It is true that if only distance and size of the optical elements are taken into consideration, the resolution increases as the distance decreases, but this is offset by the fact that as the distance decreases, the angle at which sub-images of the edges of the display screen are picked up increases more and more. This increase of the angle causes a distortion of the image, and defocus of the image because not every pixel of the image can be sharply focused. These effects also lead to a decrease of the resolution.

Preferably, the sub-images at least partly overlap each other. Sub-image overlaps have the advantage that errors can be satisfactorily localized.

Preferably, between 100 (for example, 10×10) and 1200 (for example, 40×30) sub-images are picked up per display screen. The data of each sub-image are applied to a processing unit. The time required by this processing unit to process the data and generate differences between the picked up image and the standard image (hereinafter also referred to as "processing time") should be of the order of the time which is required to adjust the mirror arrangement and the focal lens and to dampen vibrations (hereinafter also referred to as "adjusting time"). The processing time increases as the number of sub-images decreases, so that the surface of a sub-image increases. This is, however, no linear relation, but the processing time increases faster than linearly with the surface. From a point of view of processing the data, it is favorable to pick up small and many sub-images. However, a waiting time is to be observed between each pick-up operation in order to adjust the mirror arrangement and the focal lens and to dampen vibrations. It is not possible to measure during an adjusting time. For reasons of efficiency, it is therefore favorable to maintain the total adjusting time (which is equal to the number of sub-images multiplied by an adjusting time) to be short and thus to pick up a small number of images. This seems to be a dilemma. However, the inventors have realized that, if the processing time is approximately equal to or several times larger than the adjusting time, the data of a sub-image can be entirely processed or processed for the greater part while the mirror arrangement and the focal lens are being adjusted for the next sub-image, thus resulting in a very efficient method.

Except for an initial sub-image and a final sub-image, an adjacent sub-image is preferably picked up after each sub-image. Consequently, the display screen is preferably not scanned from left to right and line by line, as is common practice with electron beams in cathode ray tubes, but each sub-image (with the exception of an initial sub-image and a final sub-image) adjoins and preferably partially overlaps the previous sub-image. The optical elements (such as mirror arrangement and focal lens) thus make small movements so that the adjusting time is short and, moreover, the adjusting time between two sub-images is approximately equal for each sub-image. The total adjusting time is thus relatively short. Moreover, a comparison of sub-images is simpler and difference data can therefore be generated more rapidly.

In the method according to the invention, difference data about differences between the picked up image and the standard image are generated in the processing unit, which data are applied to a further processing unit. Since analysis takes place per sub-image and all important (difference) data are applied to the further processing unit, the processing unit needs to be provided with only a relatively small memory (as compared with a method in which the total image is picked up in one operation). This has a cost-decreasing effect and raises the speed with which measurements can take place.

The processing unit only applies those difference data which exceed a threshold value to the further processing unit.

The processing unit may apply all data to the further processing unit. However, the inventors have realized that it is more efficient to filter the difference data before they are applied to the further processing unit and to apply only differences which are larger than a threshold value. Such a filter considerably reduces the number of data to be processed.

In the further processing unit, the difference data are preferably processed, ordered as to magnitude and/or importance, and these ordered data are applied to a display device for the purpose of display. The further processing unit processes the difference data to errors in the image and orders these data as to magnitude and/or importance. The result is displayed in a display device. By displaying the image errors as to magnitude and/or importance, an operator will be able to judge these errors. In the current state of the art, this is a great advantage. Not every "error" which is displayed is necessarily a real error. A method in which inspection of the detected errors by a human being is possible thus has great advantages. The further processing unit preferably comprises a means for introducing data about errors in the image. This provides the possibility of supplying data about errors in the image to the further processing unit. This may be used, for example, for suppressing frequently recurrent "false" errors.

These and other aspects of the invention are apparent from and will be elucidated with reference to the embodiments described hereinafter.

DETAILED DESCRIPTION OF THE INVENTION

Figure 1:
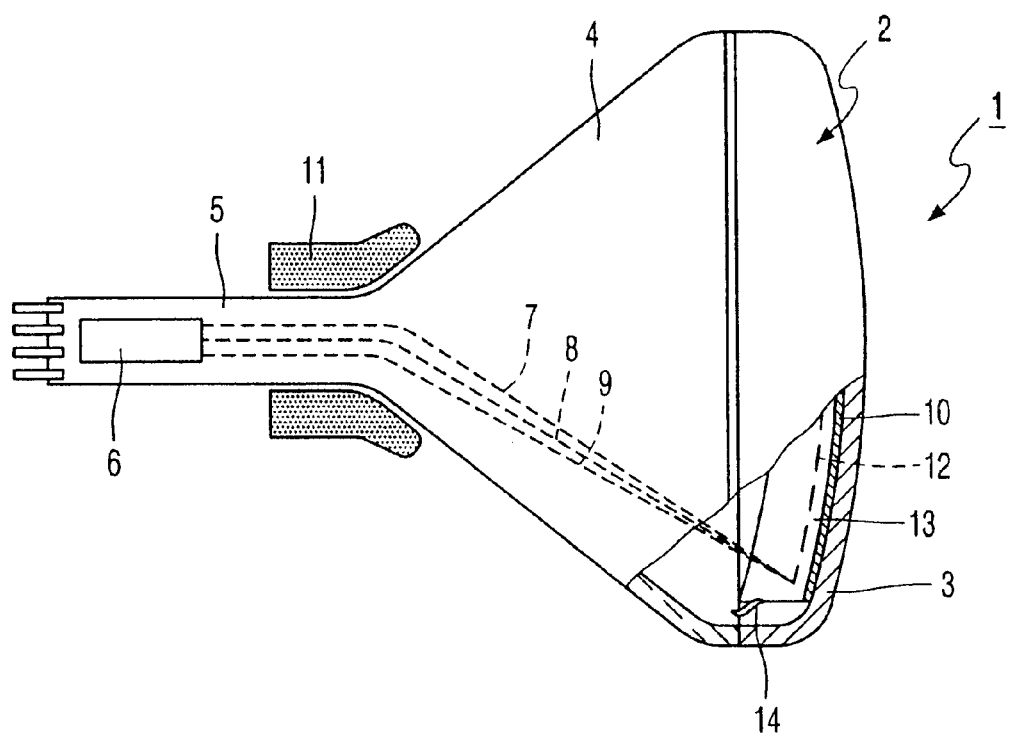
FIG. 1 shows diagrammatically a cathode ray tube.

The Figures are not drawn to scale. Generally, identical components in the Figures are denoted by the same reference numerals.

The cathode ray tube shown in FIG. 1 is a color cathode ray tube 1 with an evacuated envelope 2 comprising a display window 3, a cone 4 and a neck 5. The neck 5 accommodates an electron gun 6 for generating three electron beams 7, 8 and 9 extending, in this embodiment, in one plane, the in-line plane. A display screen 10 is present on the inner side of the display window 3. The display screen 10 comprises a plurality of phosphor elements luminescing in red, green and blue. Each group (red, green or blue) of phosphor elements forms a pattern. The display screen may also comprise other patterns such as a black matrix (a black pattern) or color filter patterns. In cathode ray tubes of the index type, patterns may be provided with index elements. On their way to the display screen 10, the electron beams 7, 8 and 9 are deflected across the display screen 10 by means of a deflection unit 11 and pass a color selection electrode 12 arranged in front of the display window 3 and having a thin plate with apertures 13. The three electron beams 7, 8 and 9 pass the apertures 13 in the color selection electrode at a small angle and thus each impinge on phosphor elements of one color. In this embodiment, the color selection electrode is suspended by suspension means 14.

The above-mentioned patterns are provided, in steps of a manufacturing method, on the display window and constitute parts of the display screen. The display window together with the display screen is secured to the cone during manufacture of a cathode ray tube, the envelope is evacuated and sealed, the deflection unit is placed and many other operations are performed. The display of an image on the display screen cannot be inspected until after the cathode ray tube has been assembled. However, if one or more of said patterns show errors, this may lead to unacceptable errors in the displayed image, resulting in rejection of the cathode ray tube because it may no longer comply with the imposed quality requirements. It is therefore important to inspect provided patterns before further manufacturing steps are taken.

Figure 2:
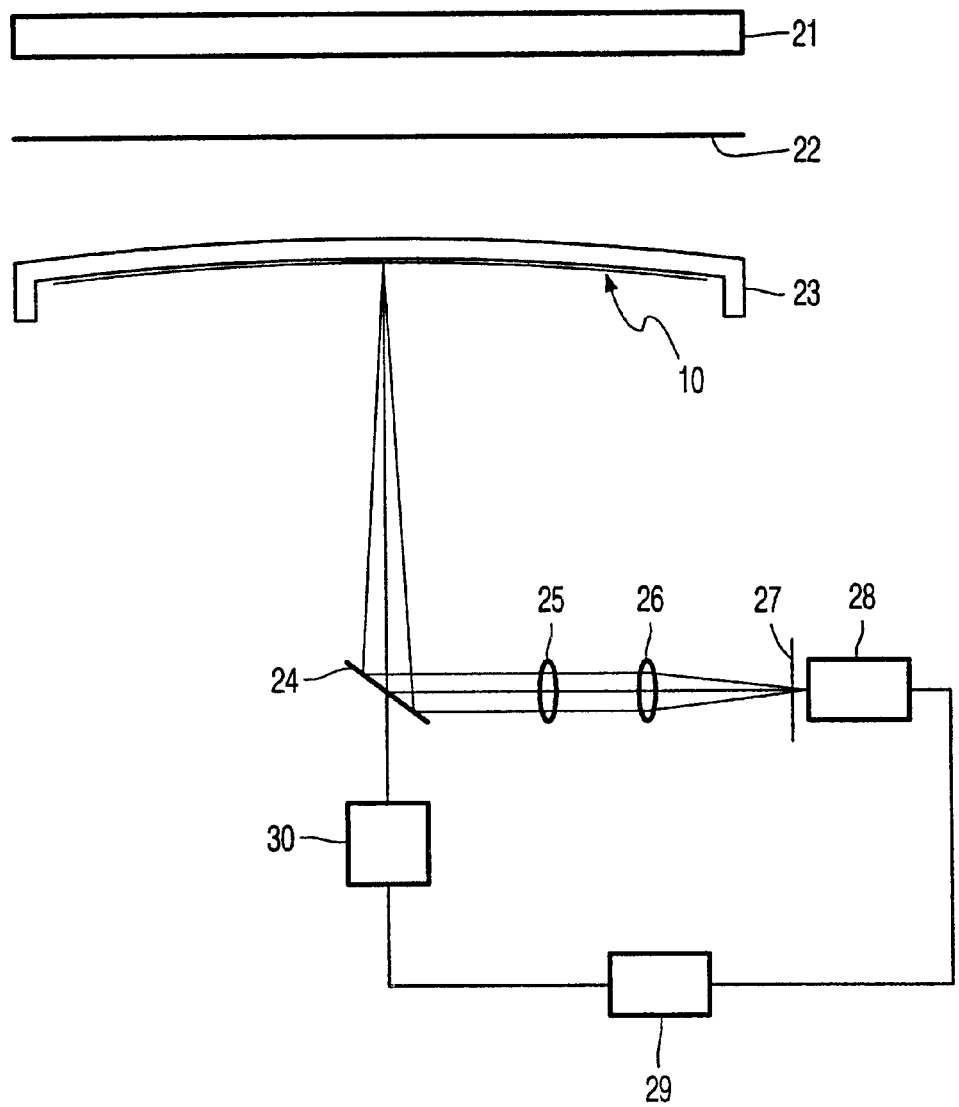
FIG. 2 shows diagrammatically an arrangement for the known method.

FIG. 2 shows an arrangement for the known method. Light source 21 illuminates, via a diffuser 22, a display window 23 whose inner side is provided with a display screen 10. This inner side is spherically curved, i.e. the radius of curvature of the inner surface is constant in all directions and at all points. Mirror 24 is present in the focus of the spherical inner surface. Light from a point is imaged via the mirror 24 and lenses 25 and 26 on an aperture in the screen 27, behind which a light meter 28 is arranged. The mirror is movable in two directions by means of a drive unit 30. The measured intensity is applied to a computer 29 which also measures and/or controls the position of the mirror. Although the light intensity for each point of the inner surface can be measured in this way and errors can be detected, the known method has a number of shortcomings. A very large number of measurements must be performed. When the mirror moves during the measurements, this will have a detrimental influence on the measurements, and when the mirror is moved only between the measurements, the total measuring time will be longer. This means that it will require a long time to measure the screen so that the method cannot be used or can hardly be used during manufacture of a cathode ray tube (in-line inspection). It is only possible to carry out random inspections. The mirror should be in the focus of the spherical inner surface. In the last few years, the inner surfaces of cathode ray tubes have, however, become flatter and flatter, with the result that the radius of curvature has increased to several meters. As the radius of curvature increases, the distance between the mirror and the inner surface should also increase in the known method. This enlarges the space occupied by the arrangement and increases the costs. Moreover, it reduces the accuracy with which measurements can be performed, which is all the more important because the patterns generally become finer and finer and the requirements imposed on accuracy therefore become more stringent. More and more use is also made of aspherical inner surfaces, i.e. inner surfaces for which the radius of curvature per point and per direction exhibits variations. The known method is less suitable for aspherical inner surfaces.

Figure 3:
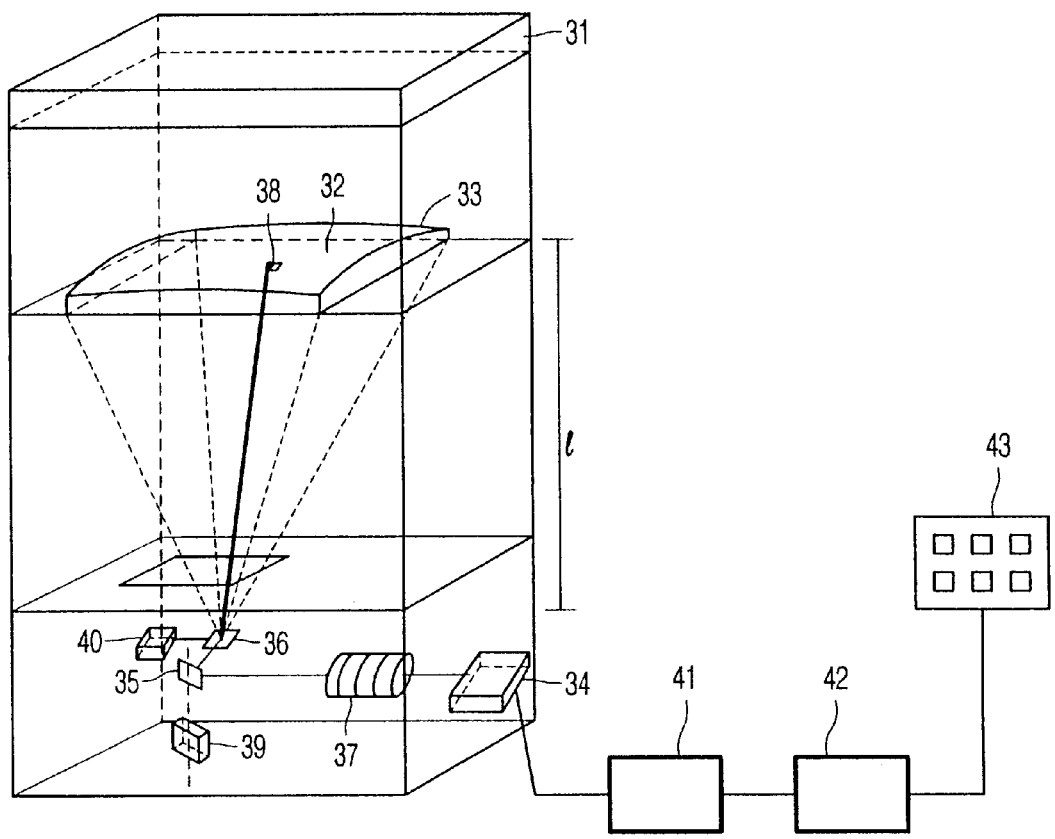
FIG. 3 shows diagrammatically an arrangement for the method according to the invention.

FIG. 3 shows diagrammatically an arrangement for a method according to the invention. A display screen 32 is illuminated on an inner side of a display window 33 by means of an illumination unit 31. Camera 34 picks up an image of a surface 38. The image of this surface is imaged on a pick-up surface of the camera (for example, a CCD array) via mirrors 35 and 36 and by means of an adjustable focal lens 37. The position of the mirrors 35 and 36 is controlled by drive units 39 and 40, respectively. Mirror 36 is at a distance 1 from the center of the display screen. This distance is preferably between 50 and 120 cm. The data are applied to a processing unit 41. During image pick-up, the mirrors and the focal lens stand still so that the measurements are not disturbed by movements of the mirrors and/or focal lens. The adjustable focal lens 37 provides the possibility of sharply focusing on each area. Preferably, the focal lens also provides the possibility of zooming so that a part of an area 38 can be subjected to a further inspection. The areas preferably overlap each other, which provides the possibility of tracking pattern errors extending across several areas.

In processing unit 41, the image of area 38 is compared with a standard. Difference data are subsequently applied to a further processing unit 42. Since only difference data are applied to the processing unit 42, less memory is required, both in unit 41 and in unit 42.

Between 100 (for example, 10×10) and 1200 (for example, 40×30) sub-images per display screen are preferably picked up.

The difference data are processed and ordered in processing unit 42. Preferably, the data are subsequently applied to a picture display device 43 which displays the errors in an ordered way (as to magnitude or importance). FIG. 3 illustrates this by way of areas in the image displayed by the display device 43. An operator can then further inspect the errors possibly via the zoom setting of the focal lens, and this a preferred embodiment. The decision about approval or rejection of the display screen is preferably taken by the operator.

FIGS. 4A to 4D illustrate diagrammatically a number of different embodiments of the method according to the invention.

The Figures show diagrammatically the positions of sub-images which are picked up during the method. In all Figures, 100 (10×10) sub-images are picked up, the sequence of the sub-images being indicated by means of the numerals 1' to 100'.

Figure 4A:
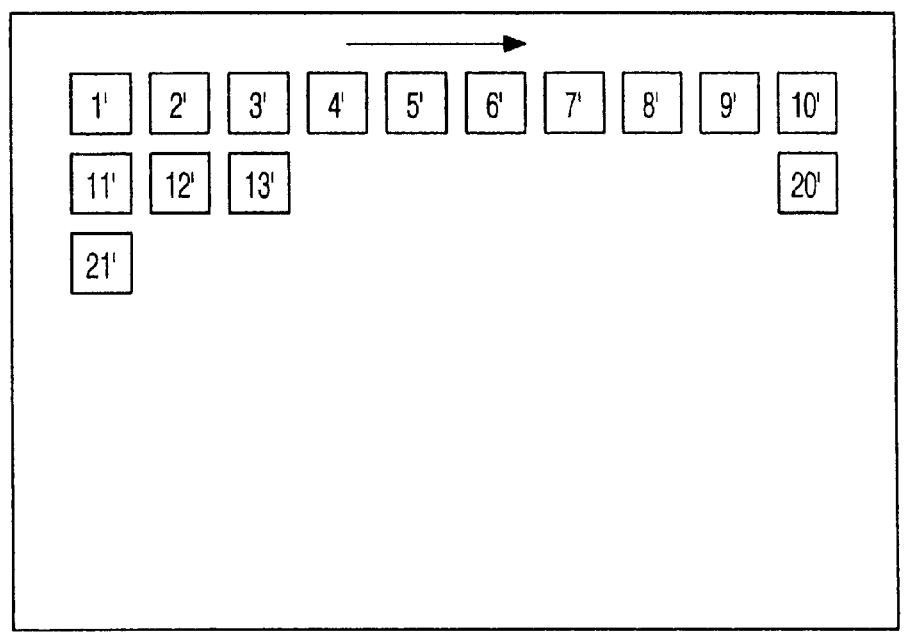
FIGS. 4A to 4D show a number of different diagrams for picking up sub-images.

In FIG. 4A, the sub-images are picked up in a sequence which corresponds to the way in which an electron beam scans a display screen in a cathode ray tube. First, a row of sub-images 1' to 10' is picked up from left to right, subsequently a row of sub-images 11' to 20' is picked up from left to right, etc. Such a method is within the scope of the invention but has the drawback that there is a much greater distance between the time-sequential sub-image 10' and 11' (and 20' and 21', etc.) than between the other time-sequential sub-images. The) differences in the adjustment of the optical elements such as lenses and mirrors are much greater between the sub-images 10' and 11' than between sub-images 9' and 10' (or 8' and 9', etc.). The adjusting time between sub-images 10' and 11' is thus much longer than that between sub-images 9' and 10'. Furthermore, the sub-images 10' and 11' do not overlap each other and are therefore not comparable with each other.

Figure 4B:
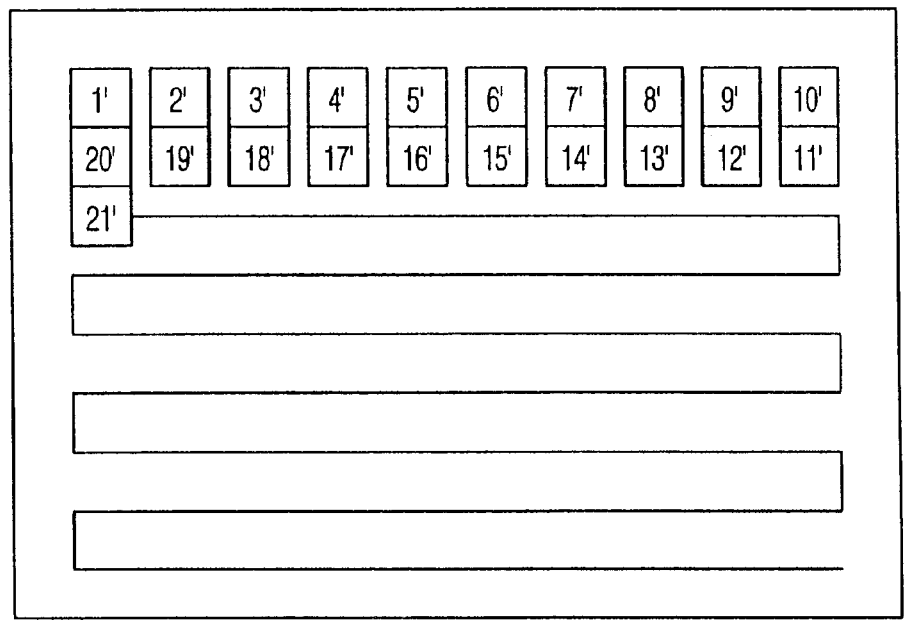
Figure 4C:
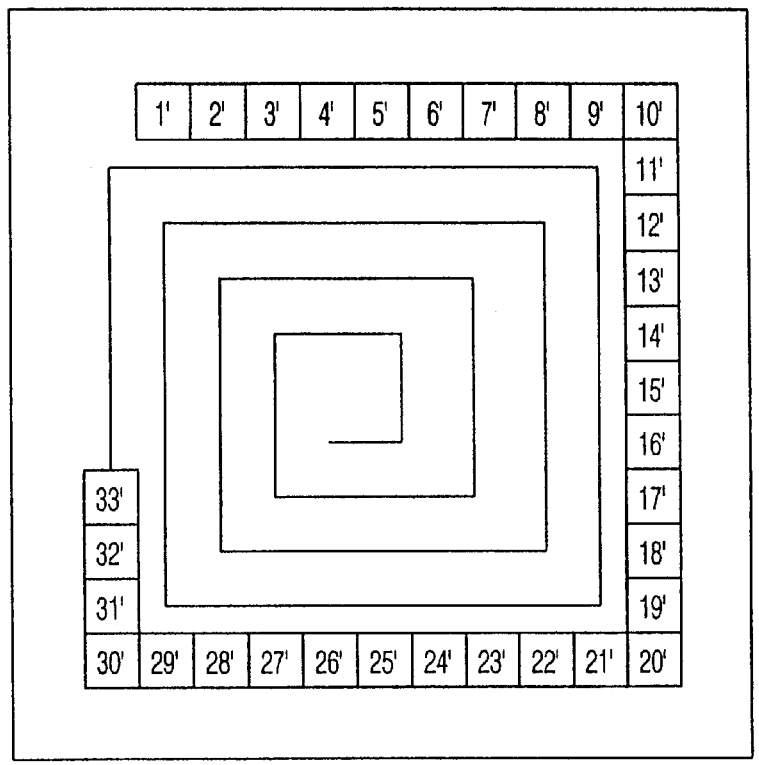
Figure 4D:
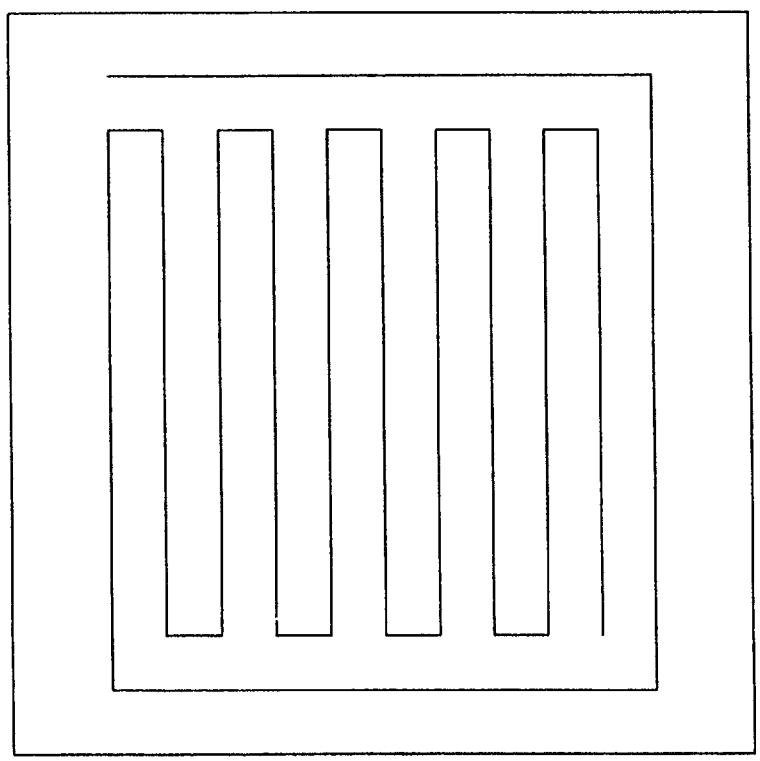

FIGS. 4B, 4C and 4D show a preferred sequence for the sub-images. In FIG. 4B, the sub-images are picked up in a zigzag sequence, in FIG. 4C in a spiral sequence and in FIG. 4D in a partially spiral sequence and partially zigzag sequence. FIGS. 4B and 4C show some sub-images and their further course by means of a line. In FIG. 4D, the course of the sub-images is illustrated by means of a line. In all of these preferred embodiments, an adjacent sub-image is picked up after each sub-image, with the exception of an initial sub-image (1') and a final sub-image (100'). The movable elements (mirrors and focal lens) only need to be moved through a small distance, which distance is also understood to be an angle. The adjusting time is relatively short and each sub-image overlaps a previous sub-image, with the exception of sub-images 1'and 100'.

Figure 5:
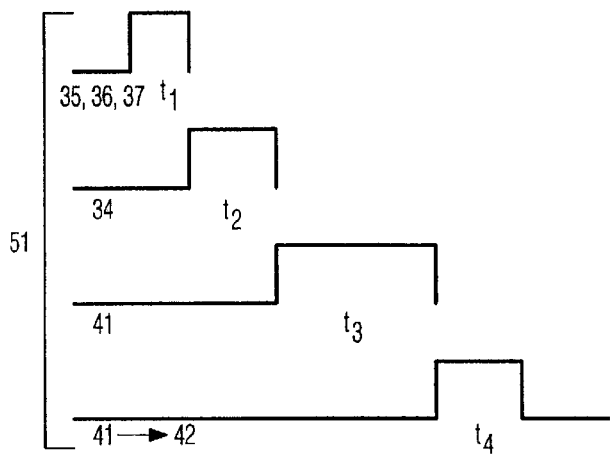
FIG. 5 illustrates diagrammatically a detail of the method.
Figure 5:
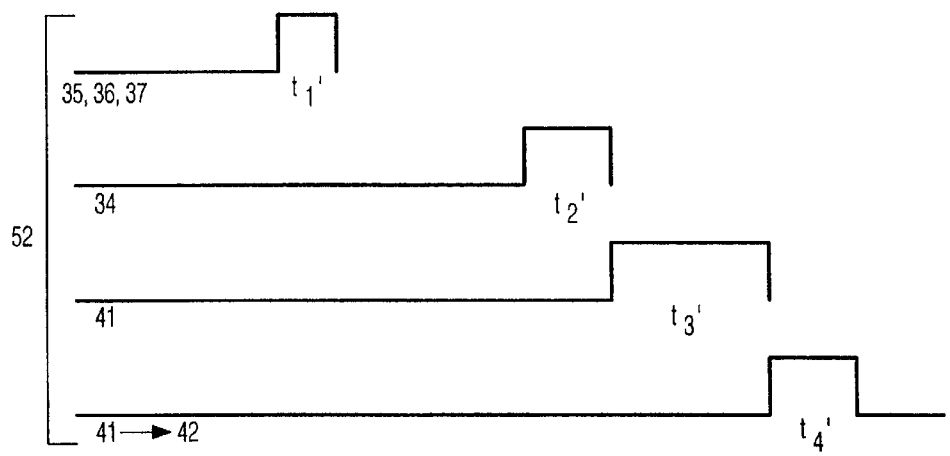

FIG. 5 shows diagrammatically which operations have to be carried out and when they have to be carried out. Sub-scheme 51 illustrates the operations for an initial sub-image and sub-scheme 52 illustrates the operations for a subsequent sub-image. Operations are denoted diagrammatically by means of blocks. It is indicated for each line which elements are active during the indicated periods of time.

During the period of time $t_1$, the mirrors (35, 36) and the focal lens (37) are adjusted in such a way that the initial sub-image can be picked up by camera 34 in period of time $t_2$. In period of time $t_3$, the data are read and the difference data are generated in unit 41. Subsequently, the difference data are applied to unit 42 in period of time $t_4$. During time $t_3$, the adjustments of the mirrors and the focal lens are changed for a subsequent sub-image, for which period of time $t'_1$, is necessary (see sub-scheme 52). Period of time $t'_2$ starts after period of time $t_4$. The movable elements 35, 36 and 37 are thus displaced (with each adjustment which may be caused by a possible change of position and/or angle or another mechanical change being denoted as "displacement") while the data are being processed (periods of time $t_3$ and/or $t_4$) but not during a measurement (period of time $t_2$). Typical values of $t_1$, $t_2$, $t_3$ and $t_4$ are 6 msec, 10–15 msec, 30–40 msec and 0–10 msec, respectively, for measurements at which several hundred sub-images are picked up and sub-images adjoin one another.

Figure 6:
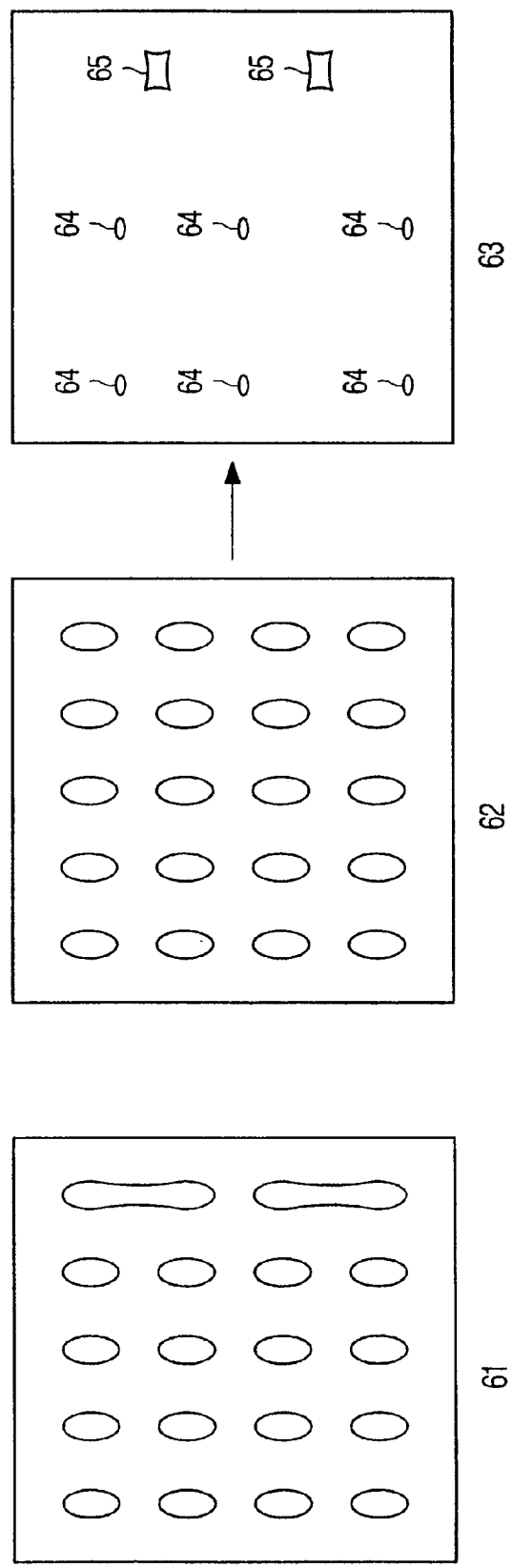
FIG. 6 illustrates diagrammatically a comparison of data.

FIG. 6 shows diagrammatically that a sub-image 61 comprising the images of some phosphor elements, is compared with a standard image 62 in unit 41, from which comparison a difference image 63 is generated, which is applied to unit 42. The total quantity of data applied to unit 42 is thus reduced considerably. The data are preferably filtered, either in unit 41 or in unit 42. In unit 42 shown in FIG. 6, the filter is, for example, adjusted in such a way that differences 64 are not passed because they are insignificant, but differences 64 are passed. A number of differences is thus detected throughout the display screen. In unit 42, these differences are ordered as to position and importance and then preferably applied to display device 43. Subsequently, an operator may or may not subject the various differences to a further inspection, for which it is useful if the focal lens has a zoom facility. It is possible that the data from more than one arrangement are applied to one and the same display device, so that an operator can operate a plurality of measuring arrangements.

In summary, the invention may be described as follows.

The display screen of a cathode ray tube is inspected. The arrangement with which the display screen is inspected comprises an adjustable mirror arrangement and an adjustable focal lens. By means of the arrangement, a set of sub-images is picked up, which sub-images are analyzed. The movable elements of the mirror arrangement and the focal lens are not moved during the image pick-up operation so as not to disturb the measurements. The difference data between picked-up images and standard images are generated in a unit, and errors are detected with reference to these difference data. These errors are preferably ordered as to magnitude and/or importance.

Some embodiments of the invention have been described hereinbefore, but it will be evident that many variations are possible within the scope of the invention.

What is claimed is:

1. A method of manufacturing a cathode ray tube, wherein the method includes inspecting a pattern provided on a display screen of or for a cathode ray tube, characterized in that the inspecting process comprises:

selecting a camera and an adjustable focal length lens which will provide a sub-image of a portion of the display screen to the camera, fixing the relative positions of the display screen, the camera and the adjustable focal length lens with respect to each other, using at least one rotatable mirror to select the portion of the display screen being viewed by the camera at any viewing instant, rotating said mirror to successive angular positions such that the camera views a corresponding succession of a multiplicity of sub-images of respectively different portions of the display, changing the focal length of the lens to bring the sub-image into focus when the distance from the mirror to the portion of the screen being viewed changes as a result of the mirror rotation, while the mirror and lens adjustment are in a rest state at each respective angular position, obtaining data descriptive of a respective picked-up sub-image in the camera, and applying the respective data of each sub-image to a processing unit.

2. A method as claimed in claim 1, further comprising the steps of: generating difference data corresponding to differences between the respective picked-up sub-image and a standard image, and applying said difference data to a further processing unit.

3. A method as claimed in claim 2, further comprising rotating the mirror to a next angular position after completion of said obtaining data corresponding to one picked-up sub-image, and before completion of applying data for said one picked-up sub-image to said further processing unit.

4. A method as claimed in claim 2, characterized in that the difference data are processed, ordered as to magnitude and/or importance in the further processing unit and in that said ordered data are applied to a display device for the purpose of display.

5. A method as claimed in claim 1, characterized in that the distance between the display screen and the mirror is between 50 cm and 120 cm.

6. A method as claimed in claim 1, characterized in that the display screen has at least one given radius of curvature, and said radius of curvature is at least 16 times the distance between the display screen and the mirror.

7. A method as claimed in claim 6, characterized in that the distance between the display screen and the mirror is between 50 cm and 120 cm.

8. A method as claimed in claim 1, characterized in that said mirror is a first mirror arranged for rotating to scan the display screen along a first axis, and the method further comprises placing a second rotatable mirror between the first mirror and the adjustable focal length lens, and rotating the second mirror to scan the display screen along a second axis orthogonal to said first axis.

9. A method as claimed in claim 1, characterized in that the sub-images at least partly overlap each other.

10. A method as claimed in claim 1, characterized in that between 100 (10×10) and 1200 (40×30) sub-images per display screen are picked up.

11. A method as claimed in claim 1, characterized in that, except for an initial sub-image and a final sub-image, a sub-image of a respectively adjacent portion of the display screen is picked up after each respective sub-image.

12. A method as claimed in claim 11, characterized in that the sub-images at least partly overlap each other.

13. A method as claimed in claim 11, further comprising rotating the mirror to a next angular position after completion of said obtaining data corresponding to one picked-up sub-image, and before completion of applying data for said one picked-up sub-image to a processing unit.

14. A method as claimed in claim 11, characterized in that between 100 (10×10) and 1200 (40×30) sub-images per display screen are picked up.

15. A method as claimed in claim 14, characterized in that the sub-images at least partly overlap each other.

16. A method as claimed in claim 15, further comprising rotating the mirror to a next angular position after completion of said obtaining data corresponding to one picked-up sub-image, and before completion of applying data for said one picked-up sub-image to a further processing unit.

* * * * *